(12) United States Patent
Manoharan et al.

(10) Patent No.: US 6,919,437 B1
(45) Date of Patent: Jul. 19, 2005

(54) SYNTHETIC METHODS AND INTERMEDIATES FOR TRIESTER OLIGONUCLEOTIDES

(75) Inventors: Muthiah Manoharan, Carlsbad, CA (US); Andrei Guzaev, Encinitas, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/329,416

(22) Filed: Jun. 10, 1999

Related U.S. Application Data

(63) Continuation-in-part of application No. 09/095,822, filed on Jun. 11, 1998, now abandoned.

(51) Int. Cl.[7] ............................................... C07H 21/00
(52) U.S. Cl. ................ 536/23.1; 536/25.31; 536/25.34; 435/6
(58) Field of Search ............................. 536/23.1, 25.31, 536/25.34; 435/6

(56) References Cited

U.S. PATENT DOCUMENTS

| | | | |
|---|---|---|---|
| 3,687,808 A | | 8/1972 | Merigan et al. |
| 4,415,732 A | | 11/1983 | Caruthers et al. |
| 4,458,066 A | | 7/1984 | Caruthers et al. |
| 4,500,707 A | | 2/1985 | Caruthers et al. |
| 4,668,777 A | | 5/1987 | Caruthers et al. |
| 4,725,677 A | | 2/1988 | Köster et al. |
| 4,973,679 A | | 11/1990 | Caruthers et al. |
| 5,132,418 A | | 7/1992 | Caruthers et al. |
| RE34,069 E | | 9/1992 | Köster et al. |
| 5,210,264 A | | 5/1993 | Yau ............................ 558/167 |
| 5,212,295 A | | 5/1993 | Cook ........................ 536/26.7 |
| 5,446,137 A | * | 8/1995 | Maag et al. ................ 536/23.1 |
| 5,770,713 A | | 6/1998 | Imbach et al. ............. 536/22.1 |
| 5,955,591 A | * | 9/1999 | Imbach et al. ............. 536/23.1 |
| 6,124,445 A | * | 9/2000 | Imbach et al. ............. 536/23.1 |
| 6,166,197 A | * | 12/2000 | Cook et al. ................. 536/24.5 |
| 6,531,590 B1 | * | 3/2003 | Manoharan et al. ...... 536/25.34 |

FOREIGN PATENT DOCUMENTS

| | | | |
|---|---|---|---|
| EP | 0 095 294 A1 | | 11/1983 |
| EP | 0095294 | * | 11/1983 |
| EP | 0 095 294 | * | 11/1983 |
| EP | 0216357 | * | 4/1987 |
| EP | 0 216 357 | * | 4/1987 |
| EP | 0 216 357 A2 | | 4/1987 |
| FR | 2540122 | * | 8/1984 |
| FR | 2540122 A1 | * | 8/1984 |
| FR | 2568254 A1 | * | 1/1986 |
| FR | 2568254 | * | 1/1986 |
| JP | 56-113794 | * | 9/1981 |
| JP | 56113794 | * | 9/1981 |
| JP | 59-36696 | | 2/1984 |
| JP | 59-036696 | * | 2/1984 |
| JP | 59036696 | * | 2/1984 |
| JP | 62-70392 | | 3/1987 |
| JP | 62070392 | * | 3/1987 |
| JP | 62-070392 | * | 3/1987 |
| JP | 62-84097 | | 4/1987 |
| JP | 62-084097 | * | 4/1987 |
| JP | 62084097 | * | 4/1987 |
| JP | 63222184 | * | 9/1988 |
| JP | 63-222184 | * | 9/1988 |
| JP | 7-25887 | | 1/1995 |
| JP | 07025887 | * | 1/1995 |
| JP | 07-025887 | * | 1/1995 |
| WO | WO 93/12132 | | 6/1993 |
| WO | WO 97/47637 | | 12/1997 |

OTHER PUBLICATIONS

Hayakawa et al. (I), "Preparation of Short Oligonucleotides via the Phosphoramidite Method Using a Tetrazole Promoter in a Catalytic Manner," *J. American Chemical Society*, 119(49), 11758–11762 (Dec. 10, 1997).*

Sakurai et al., "Synthesis of a Nucleoside Hapten with a [P(O)–O–N] Linkage to Elicit Catalytic Antibodies with Phosphodiesterase Activity," *Bioorganic& Medicinal Chemistry Letters*, 6(9), 1055–1060 (May 7, 1996).*

Bergmann et al., "Allyl as Internucleotide Protecting Group in DNA Synthesis to be Cleaved Off by Ammonia," *Tetrahedron*, 51(25), 6971–6976 (Jun. 19, 1995).*

Hayakawa et al. (II), "A General Approach to Nucleoside 3'– and 5'–Monophosphates," *Tetrahedron Letters*, 28(20), 2259–2262 (1987).*

Hayakawa et al. (II), "The Allylic Protection Method in Solid–Phase Oligonucleotide Synthesis. An Efficient Preparation of Solid–Anchored DNA Oligomers," *J. American Society*, 112(5), 1691–1696 (Feb. 28, 1990).*

Hayakawa et al. (IV), "Allyl Protection of Internucleotide Linkage," *Tetrahedron Letters*, 26(52), 6505–6508 (1985).*

(Continued)

*Primary Examiner*—James O. Wilson
*Assistant Examiner*—L. E. Crane
(74) *Attorney, Agent, or Firm*—Isis Patent Department Woodcock Washburn LLP

(57) ABSTRACT

Methods for the preparation of oligonucleotides having bioreversible phosphate blocking groups are disclosed. In one aspect, the present invention provides compounds comprising a sequence of nucleotide units that includes a first segment having at least one internucleoside linkage of formula:

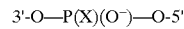

and a second segment having at least one internucleoside linkage of formula:

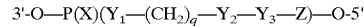

wherein each of X, $Y_1$, and $Y_2$ is, independently, O or S; q is 2 to about 4; $Y_3$ is C(=O) or S; and Z is aryl having 6 to about 14 carbon atoms or alkyl having from one to about six carbon atoms.

9 Claims, 4 Drawing Sheets

OTHER PUBLICATIONS

Hayakawa et al. (V), "Allyloxycarbonyl Group: A Versatile Blocking Group for Nucleotide Synthesis," *Journal of Orgnaic Chemistry*, 51(12), 2400–2402 (Jun. 13, 1986).*

Hayakawa et al. (VI), "Allyl and Allyloxcarbonyl Groups as Versatile Protecting Groups in Nucleotide Synthesis," paper given at the *Fourteenth Symposium on Nucleic Acids Chemistry*, Tokushima, Japan, Oct. 30, 1986, published in *Nucleic Acids Symposium Series, No. 17*, IRL Press (publ.), Oxford, England, pp. 97–100, 1986.*

Stec et al., "Automated Solid–Phase Synthesis, Separation, and Stereochemistry of Phosphorathioate Analogues of Oligodeoxyribonucleotides," *J. American Chemical Society*, 106(20), 6077–6079 (Oct. 3, 1984).*

Froehler et al., "Synthesis of DNA via Deoxynucleoside H–Phosphonate Intermediates," *Nucleic Acids Research*, 14(13), 5399–5407 (Jul. 11, 1986).*

D. W. A. Sharp (ed.), *The Penguin Dictionary of Chemistry, 2nd Edition*, Penguin Putnam Inc., New York, NY, 1990, see the definition of "silicon hydrides" at p. 359, col. 2.*

Hayakawa et al. (I), "Preparation of Short Oligonucleotides via the Phosphoramidite Method Using a Tetrazole Promoter in a Catalytic Manner," *J. American Chemical Society*, 119(49), 11758–11762 (Dec. 10, 1997).*

Barber I. et al., "The Prooligonucleotide Approach I: Esterase–Mediated Reversibility of Dithymidine S–Alkyl–Phosphorothiolates to Dithymidine Phosphorothioates," *Bioorganic&Medicinal Chem.Letters*, 1995, 5, pp. 563–568. (Mar. 16, 1995).

Mignet, N. et al., "Synthesis and Evaluation of Glucuronic Acid Derivatives as Alkylating Agents for the Reversible Masking of Internucleoside Groups of Antisense Oligonucleotides," *Carbohydrate Reseach*, 1997, 303, pp. 17–24, (Aug. 25, 1997).

Tosquellas, G. et al., "The pro–oligonucleotide approach: Solid Phase Synthesis and Preliminary Evaluation of Model Pro–dodecathymidylates", *Nuc. Acids Research*, 1998, 26, pp. 2069–2074, (Issue No. 9; May 1, 1998).

Tosquellas, G. et al., "The Prooligonucleotide Approach.III: Synthesis and Bioreversibility of a Chimeric Phosphorodithioate Prooligonucleotide", *Biorg.&Med. Chem. Letters*, 1996, 6, pp. 457–462. (issue No. 4; Feb. 20, 1996).

Weisler, Wm. et al, "Synthesis of Phosphorodithioate DNA via Sulfer–Linked, Base–Labile Protecting Groups",*J. Org. Chem.*, 1996, 61, pp. 4272–4281,((13); Jun. 28, 1996).

Alul, R.H. et al., "Oxalyl–CPG: a labile support for synthesis of sensitive oligonucleotide derivatives",*Nuc. Acid Res.*, 1991, 19, 1527–1532 (Iss. No. 7).

Bannwarth, W., "Synthesis of Oligodeoxynucleotides by the Phosphite–Triester Method Using Dimer Units and Different Phosphorous–Protectig Groups", *Helvetica Chim. Acta*, 1985, 68, 1907–1913.

Beaucage, S.L. et al., "Advances in the Synthesis of Oligonucleotides by the Phosphoramidite Approach", *Tetrahedron*, 1992, 48, 2223–2311.

Bergmann, F. et al., "Allyl as Internucleotide Protecting Group in DNA Synthesis to be Cleaved off by Ammonia," *Tetrahedron*, 1995, 51(25), 6971–6976 (Jun. 19, 1995).

Bielinska, A. et al., "Regulation of Gene Expression with Double–Stranded Phosphorothioate Oligonucleotides", *Science*, 1990, 250, 997–1000 (Nov. 16, 1990).

Cook, P.D., "Medicinal chemistry of antisense oligonucleotides—future opportunities", *Anti–Cancer Drug Design*, 1991, 6, 585–607.

Crooke, S.T., "Nucleic Acid Therapeutics", in *Pharmaceutcal Manufacturing International: The International Review of Pharmaceutical Technology Research and Development*, Sterling, London, Barnacal, P.A. (ed.), 1992, 4 pages.

Crooke, S.T. et al., "Progress in Antisense Oligonucleotide Therapeutic", *Ann. Rev. Pharmacol. Toxicol.*, 1996, 36, 107–129.

Delgado, C. et al., "The Uses and Properties of PEG–Linked Proteins", *Crit. Rev. in Therapeutic Drug Carrier Sys.*, 1992, 9, 249–304 (Issue 3–4).

Englisch, U. et al., "Chemically Modified Oligonucleotides as Probes and Inhibitors",*Angew. Chem. Int. Ed. Eng.*, 1991, 30, 613–629 (Iss. No. 6, Jun. 1991).

Hayakawa, Y. et al., "The Allylic Protection Method in Solid–Phase Oligonucleotide Synthesis. An Efficient Preparation of Solid–Anchored DNA Oligomers," *J. Am. Chem. Soc.*, 1990, 112, 1691–1696 (Iss. No. 5; Feb. 28, 1990).

Hayakawa, Y. et al., "Preparation of Short Oligonucleotides via the Phosphoramidite Method Using a Tetrazole Premoter in a Catalytic Manner," *J. Am. Chem. Soc.*, 1997, 119, 11758–11762 (Issue No. 49; Dec. 10, 1997).

Hayakawa, Y. et al., "A General Approach to Nucleoside 3' –and 5'–Monophosphates," *Tetra. Lett.*, 1987, 28(20), 2259–2262.

Hayakawa, Y. et al., "Allyl Protection of Internucleotide Linkage," *Tetra. Lett.*, 1985, 26(52), 6505–6508.

Hayakawa, Y. et al., "Allyl and Allyloxycarbonyl Groups as Versatile Protecting Groups in Nucleotide Synthesis," paper given at the Fourteenth Symposium in Nucleic Acids Chemistry, Tokushima, Japan, Oct. 30, 1986, published in *Nucl. Acids Symp. Series*, 1986, No. 17, 97–100.

Hayakawa, Y. et al., "Allyloxycarbonyl Group: A Versatile Blocking Group for Nucleotide Synthesis," *J. Org. Chem.*, 1986, 51(12), 2400–2402 (Jun. 13, 1986).

Iyer et al., "Bioreversible Oligonucleotide Conjugates by Site–Specific Derivatization", *Bioorg. Med. Chem. Lett.*, 1997, 7(7), 871–876.

Iyer et al., "*N*–pent–4–enoyl (*PNT*) as a Universal Nucleobase Protecter: Applications in the Rapid and Facile Synthesis of Oligonucleotides, Analogs, and Conjugates", *Tetrahedron*, 1997, 53(8), 2731–2750.

Kroschwitz, J.I., "Polynucleotides", *Concise Encyclopedia of Polymer Science and Engineering*, 1990, John Wiley & Sons, New York, 858–859.

Kumar, G. et al., "Improvements in Oligodeoxyribonucleotide Synthesis: Methyl N,N–Dialkylphoramidite Dimer Units for Solid Support Phosphite Methodology", *J. Org. Chem.*, 1984, 49, 4905–1912 (Issue No. 25).

Mignet et al., "The Pro–Oligonucleotide Approach. V: Influence of the Phosphorus Atom Environment on the Hydrolysis of Enzymolabile Dinucleoside Phosphotriesters", *Bioorg. Med. Chem. Lett.*, 1997, 7(7), 851–854.

Milligan et al., "Current Concepts in Antisense Drug Design", *J. Med. Chem.*, 1993, 36(14), 1923–1937 (Jul. 9, 1993).

Miura, K. et al., "Blockwise Mechanical Synthesis of Oligonucleotides by the Phosphoramidite Method", *Chem Pharm. Bull.*, 1987, 35, 833–836 (Iss. No. 2).

Ouchi, T. et al., "Synthesis and Antitumor Activity of Poly(Ethylene Glycol)s Linked to 5'–Fluorouracil via a Urethane or Urea Bond", *Drug Des. & Disc.*, 1992, 9, 93–105.

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.*, 1991, 56, 4329–4333 (Issue No. 13).

Sakurai, M. et al., "Synthesis of a Nucleoside Hapten with a [P(O)–O–N] Linkage to Elicit Catalytic Antibodies with Phosphodiesterase Activity," *Bioorg. Med. Chem. Lett.*, 1996, 6(9), 1055–1060 (May 7, 1996).

Sanghvi, Y.S., "Heterocyclic Base Modifications in Nucleic acids and their Applications in Antisense Oligonucleotides", *Antisense Research and Applications*, Crooke et al. (Eds.), CRC Press, Boca Raton, 1993, *Chapter 15*, 273–288.

Secrist, J.A. et al., "Synthesis and Biological Activity of 4'–Thionucleosides", *10th International rountable: Nucleosides, Nucleotides and their Biological Applications*, Sep. 16–20, 1992, *Abstract 21*, Park City, Utah, 40.

Spiller et al., "The uptake kinetics of chimeric oligodeoxynucleotide analogues in human leukaemia MOLT–4 cells", *Anti–Cancer Drug Design*, 1992, 7, 115–129.

Tosquellas et al., "The Prooligonucleotide Approach IV: Synthesis of Chimeric Prooligonucleotides with 6 Enzymolabile Masking Groups and Unexpected Desulfurization Side Reaction", *Bioorg. Med. Chem. Lett.*, 1997, 7(3), 263–268.

Uhlmann, E. et al., "Antisense Oligonucleotides: A New Therapeutic Principle", *Chem. Reviews*, 1990, 90, 544–584 (Issue No. 4; Jun., 1990).

Varma, "Synthesis of Oligoncleotide Analogues with Modified Backbones", *Synlett*, 1993, 621–637 (Sep., 1993).

Wolter, A. et al., Polymer Support Oligonucleotide Synthesis XX: Synthesis of a Henhectacosa Deoxynucleotide by use of a Dimeric Phosphoramidite *Nucleosides & Nucleotides*, 1986, 5, 65–77 Issue No. 1).

Wright, P. et al., "Large Scale Synthesis of Oligonucleotides via phosphoramidite (Iss. No. 21) Nucleosides and a High–loaded Polystyrene Support", *Tetra. Letts.*, 1993, 34, 3373–3376.

Wu, H. et al., "Inhibition of in vitro transcription by specific double–stranded oligodeoxyribonucleotides", *Gene*, 1990, 89, 203–209.

Pon, R.T. et al., "Hydroquinone–O, O–diacetic acid ('Q–linker') as a replacement for succinyl and oxalyl linker arms in solid phase oligonucleotide synthesis," *Nucl. Acids Res.*, 1997, 25(18), 3629–3635.

Sinha et al., "Labile exocyclic amine protection of nucleosides in DNA, RNA and oligonucleotide analog synthesis facilitating N–deacylation, minimizing depurination and chain degradation," *Biochimie*, 1993, 75, 13–23.

Wu et al., "N–Phenoxyacetylated Guanosine and Adenosine Phosphoramidites in the Solid Phase Synthesis of Oligoribonucleotides: Synthesis of a Ribozyme Sequence," *Tetra. Lett.*, 1988, 29(34), 4249–4252.

Barber I. et al., "The Prooligonucleotide Approach I: Esterase–Mediated Reversibility of Dithymidine S–Alkyl–Phosphorothiolates to Dithymidine Phosphorothioates," *Bioorganic&Medicinal Chem.Letters*, 1995, 5, pp. 563–568, (Mar. 16, 1995).

Mignet, N. et al., "Synthesis and Evaluation of Glucuronic Acid Derivatives as Alkylating Agents for the Reversible Masking of Internucleoside Groups of Antisense Oligonucleotides," *Carbohydrate Research*, 1997, 303, pp. 17–24. (Aug. 25, 1997).

Tosquellas, G. et al., "The pro–oligonucleotide approach: Solid Phase Synthesis and Preliminary Evaluation of Model Pro–dodecathymidylates", *Nuc. Acids Research*, 1998, 26, pp. 2069–2074. (Issue No. 9; May 1, 1998).

Tosquellas, G. et al., "The Prooligonucleotide Approach.III: Synthesis and Bioreversibility of a Chimeric Phosphorodithioate Prooligonucleotide", *Biorg.&Med. Chem. Letters*, 1996, 6, pp. 457–462. (issue No. 4; Feb. 20, 1996).

Weisler, Wm. et al, "Synthesis of Phosphorodithioate DNA via Sulfur–Linked, Base–Labile Protecting Groups", *J. Org. Chem.*, 1996, 61, pp. 4272–4281.((13); Jun. 28, 1996).

* cited by examiner

2M Et₂NH/Dioxane or 1 M piperidine/MeCN  DCA/DCM
4 hours at room temperature 1. 0.05M K₂CO₃/ MeOH; 80 min/RT
2. Dowex 50Wx8 pyH⁺

1: M = H₃C—O—(dimethoxyphenyl)

2: M = O

Linkages 1 and 2 to solid support dA$^{ceoc}$ and dC$^{ceoc}$ phosphoramidites

2M Et₂N H/Dioxane or 1 M piperidine/MeCN DCA/DCM
8-12 hours at room temperature 1. 0.01M K₂CO₃/ MeOH; 80 min/RT
2. AcOH or Dowex 50Wx8 pyH⁺

Oligonucleotide # 1    5

Nu = nucleoside (mixed bases)
M = O or
M =

SEQUENCE LISTING

<160> NUMBER OF SEQ ID NOS: 4

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: antisense
      sequence

<400> SEQUENCE: 1
tttttttttt t                                                          11

<210> SEQ ID NO 2
<211> LENGTH: 12
<212> TYPE: DNA
<213> ORGANISM: Artificial Sequence
<220> FEATURE:

```
<223> OTHER INFORMATION: Description of Artificial Sequence: antisense
      sequence

<400> SEQUENCE: 2 ttttttttt tt                                                          12

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: antisense
      sequence

<400> SEQUENCE: 3 ttttttttt ttttttttt                                                   19

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: antisense
      sequence

<400> SEQUENCE: 4
cccccaattt tttttttt                                                   18
```

SYNTHETIC METHODS AND INTERMEDIATES FOR TRIESTER OLIGONUCLEOTIDES

CROSS REFERENCE TO RELATED APPLICATIONS

This application is a continuation-in-part of U.S. Ser. No. 09/095,822 filed Jun. 11, 1998, now abandoned the contents of which is incorporated by reference herein in its entirety.

FIELD OF THE INVENTION

This invention is directed to methods for the preparation of protected forms of oligonucleotides wherein at least one of the phosphate moieties of the oligonucleotide is protected with a protecting group that is removable by intracellular enzymes. The methods of the invention can be used to prepare prodrug forms of oligonucleotides and chimeric oligonucleotides that are modified with certain functional groups that are cleavable by intercellular enzymes to release the oligonucleotide from its prodrug form. The oligonucleotides prepared by the methods of the invention can be of any known sequence, preferably one that is complementary to a target strand of a mRNA. The compounds produced by the methods of the invention are useful for therapeutics, diagnostics, and as research reagents.

BACKGROUND OF THE INVENTION

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or other-wise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as such antisense agents in human clinical trials for various disease states, including use as antiviral agents.

Transcription factors interact with double-stranded DNA during regulation of transcription. Oligonucleotides can serve as competitive inhibitors of transcription factors to modulate their action. Several recent reports describe such interactions (see Bielinska, et. al., *Science* 1990, 250, 997–1000; and Wu, et. al., *Gene* 1990, 89, 203–209).

In addition to such use as both indirect and direct regulators of proteins, oligonucleotides and their analogs also have found use in diagnostic tests. Such diagnostic tests can be performed using biological fluids, tissues, intact cells or isolated cellular components. As with gene expression inhibition, diagnostic applications utilize the ability of oligonucleotides and their analogs to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides and their analogs are also widely used as research reagents. They are useful for understanding the function of many other biological molecules as well as in the preparation of other biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides and their analogs, both natural and synthetic, are employed as primers in such PCR technology.

Oligonucleotides and their analogs are also used in other laboratory procedures. Several of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual*, supra. See also "DNA-protein interactions and The Polymerase Chain Reaction" in Vol. 2 of *Current Protocols In Molecular Biology*, supra.

Oligonucleotides and their analogs can be synthesized to have customized properties that can be tailored for desired uses. Thus a number of chemical modifications have been introduced into oligomeric compounds to increase their usefulness in diagnostics, as research reagents and as therapeutic entities. Such modifications include those designed to increase binding to a target strand (i.e. increase their melting temperatures, Tm, to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once sequence-specifically bound to a target, and to improve the pharmacokinetic properties of the oligonucleotide.

The complementarity of oligonucleotides has been used for inhibition of a number of cellular targets. Such complementary oligonucleotides are commonly described as being antisense oligonucleotides. Various reviews describing the results of these studies have been published including Progress In Antisense Oligonucleotide Therapeutics, Crooke, S. T. and Bennett, C. F., *Annu. Rev. Pharmacol.*

Toxicol., 1996, 36, 107–129. These oligonucleotides have proven to be very powerful research tools and diagnostic agents. Further, certain oligonucleotides that have been shown to be efficacious are currently in human clinical trials.

It is well known, however, that oligonucleotides and their phosphorothioate analogues are of limited stability in blood and tissues. Also, since such compounds are being negatively charged they lack the ability to efficiently permeate biological membranes. Thus, both their oral bioavailability and cellular uptake are usually low. To overcome this problem, several types of modified oligonucleotides have been introduced. Among such oligonucleotides, backbone modified neutral oligonucleotides (namely, methylphosphonates and phosphate triester analogs) have gained a wide recognition. Recently, the latter modification has been even further developed with the introduction of bioreversible phosphate protecting groups into synthetic oligonucleotides. (see, e.g., Tosquellas, et al., *Bioorg. Med. Chem. Lett.* 1997, 7, 263; Mignet, et al.,*Bioorg. Med. Chem. Lett.* 1997, 7, 851; Iyer, et al., *Bioorg. Med. Chem. Lett.* 1997, 7, 871; Iyer, et al., *Tetrahedron* 1997, 53, 2731). These groups are cleaved in a two-step process where the first step is either enzyme- or base-catalyzed hydrolysis of a (thio)ester group. The intermediate thus formed is unstable and spontaneously decomposes in neutral or slightly basic media to restore parent phosphorothioate diester and release either episulfide or quinonemethyde as a byproduct.

The synthesis of oligonucleotides with bioreversible phosphate protecting groups is complicated by the fact that one must deprotect phosphate and nucleic base moieties (typically by treatment with a base) while keeping the base labile (thio)ester function of the prodrug moiety intact. To a limited extent, this problem has been addressed with the (4-acyloxyphenyl)methyl group by finding more stable acyl residues and applying milder deprotection conditions. (see, Iyer, et al., supra). No selective deprotection method has yet to be reported, however, for the highly base-labile S-acyl 2-mercaptoethyl (SATE) group. Indeed, the reported synthesis for oligonucleotides having both phosphodiester and SATE phosphotriester units have involved postsynthetic alkylation of phosphorothioate oligonucleot Accordingly, there still remains a need for synthetic techniques and intermediates for such oligonucleotides, particularly techniques that do not involve postsynthetic modifications.

SUMMARY OF THE INVENTION

The present invention is directed to methods for the preparation of phosphodiester-containing oligonucleotides having at least one bioreversible protecting group that confers enhanced chemical and biophysical properties. The bioreversible protecting groups lend nuclease resistance to the oligonucleotides and are removed in a cell, in the cell cytosol, or in vitro in cytosol extract, by endogenous enzymes. In certain preferred oligonucleotides of the invention the bioreversible protecting groups are designed for cleavage by carboxyesterases to yield unprotected oligonucleotides.

In one aspect, the present invention provides compounds comprising a sequence of nucleotide units that includes a first segment having at least one phosphodiester internucleoside linkage of formula:

3'-O—P(X)(O⁻)—O-5' and a second segment having at least one phosphotriester internucleoside linkage of formula:

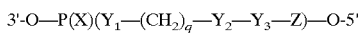

wherein each of X, $Y_1$, and $Y_2$ is, independently, O or S; q is 2 to about 4; $Y_3$ is C(=O) or S; and Z is aryl having 6 to about 14 carbon atoms or alkyl having from one to about six carbon atoms. In preferred embodiments, a predetermined number of nucleoside units separate the linkages of the first and second segments. Particularly preferred compounds are those comprising a moiety having Formula I:

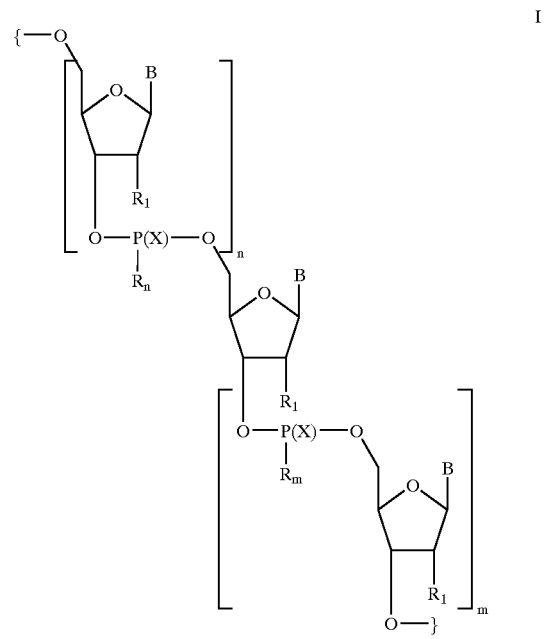

wherein:
  each B is, independently, a naturally occurring or non-naturally occurring nucleobase;
  each $R_1$ is, independently, H, OH, F, or a group of formula $R_7$—$(R_8)_n$;
  each $R_7$ is, independently, $C_3$–$C_{20}$ alkyl, $C_4$–$C_{20}$ alkenyl, $C_2$–$C_{20}$ alkynyl, $C_1$–$C_{20}$ alkoxy, $C_2$–$C_{20}$ alkenyloxy, or $C_2$–$C_{20}$ alkynyloxy;
  each $R_8$ is, independently, hydrogen, amino, protected amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, a group that enhances the pharmacokinetic properties of oligonucleotides, or a group of formula (—O—$X_3$)$_p$, where p is 2 to about 10 and $X_3$ is alkyl having from one to about 10 carbons;
  each X is, independently, O or S;
  n is 1 to about 100 (preferably about 2 to about 25);

m is 1 to about 100 (preferably about 2 to about 25); and $R_n$ and $R_m$ are selected such that:

each $R_n$ is, independently, $O^-$ or $O$—$(CH_2)_p$—E and each $R_m$ is —$Y_1$—$(CH_2)_q$—$Y_2$—$Y_3$—Z; or each $R_n$ is —$Y_1$—$(CH_2)_q$—$Y_2$—$Y_3$—Z and each $R_m$ is, independently, $O^-$ or $O$—$(CH_2)_p$—E;

wherein:

p is 1 to about 5 (preferably 2);

E is a group that is electron-withdrawing with respect to hydrogen (preferably CN); and each $Y_1$, $Y_2$, $Y_3$, q, and Z are, independently, as defined above.

Such compounds are generally prepared by contacting a starting compound of Formula II with a secondary amine compound in an organic solvent:

wherein B, $R_1$, X, $R_n$, $R_m$, n, and m are as defined above (provided that at least one of said $R_n$ and $R_m$ is $O$—$(CH_2)_p$—E); $R_z$ is aryl having about 5 to about 8 carbon atoms or has formula $(CH_2)_{x3}$; z is 0 or 1; $x_1$, $x_2$, and $x_3$ are, independently, 1 to about 5; $R_{N1}$ is H or alkyl having 1 to about 10 carbon atoms; $R_{N2}$ is a solid support; and at least one $R_n$ or $R_m$ is $O$—$(CH_2)_p$—E. This contacting is performed for a time and under conditions effective to produce an intermediate compound of Formula II wherein the at least one $R_n$ or $R_m$ is $O^-$. This intermediate compound is then contacted with a mild base in an organic solvent under conditions effective to produce a product having Formula III:

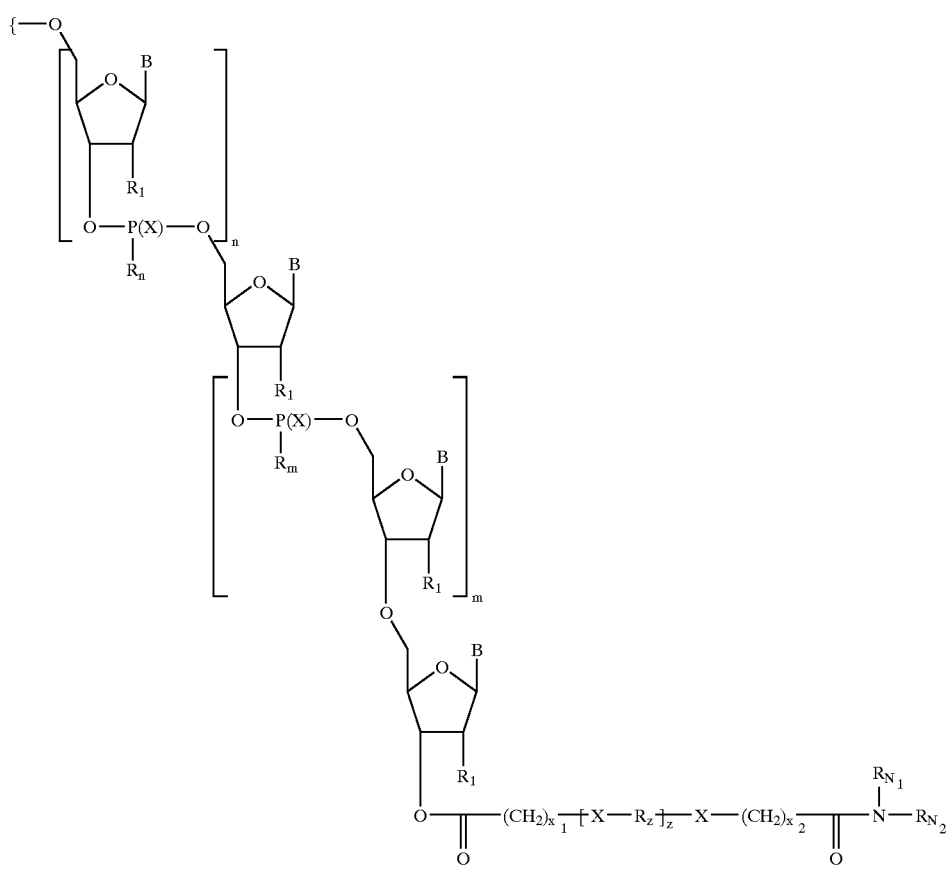

II

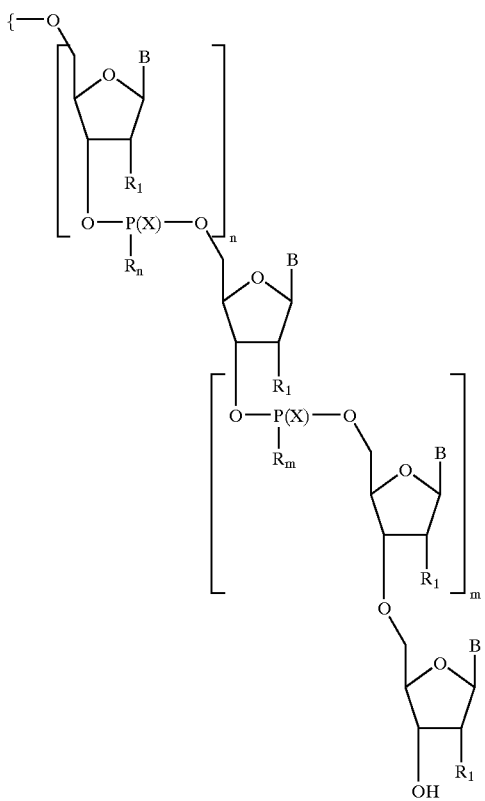

III

BRIEF DESCRIPTION OF THE DRAWINGS

The numerous objects and advantages of the present invention may be better understood by those skilled in the art by reference to the accompanying non-scale figures, in which.

DETAILED DESCRIPTION OF THE INVENTION

Figure 1:
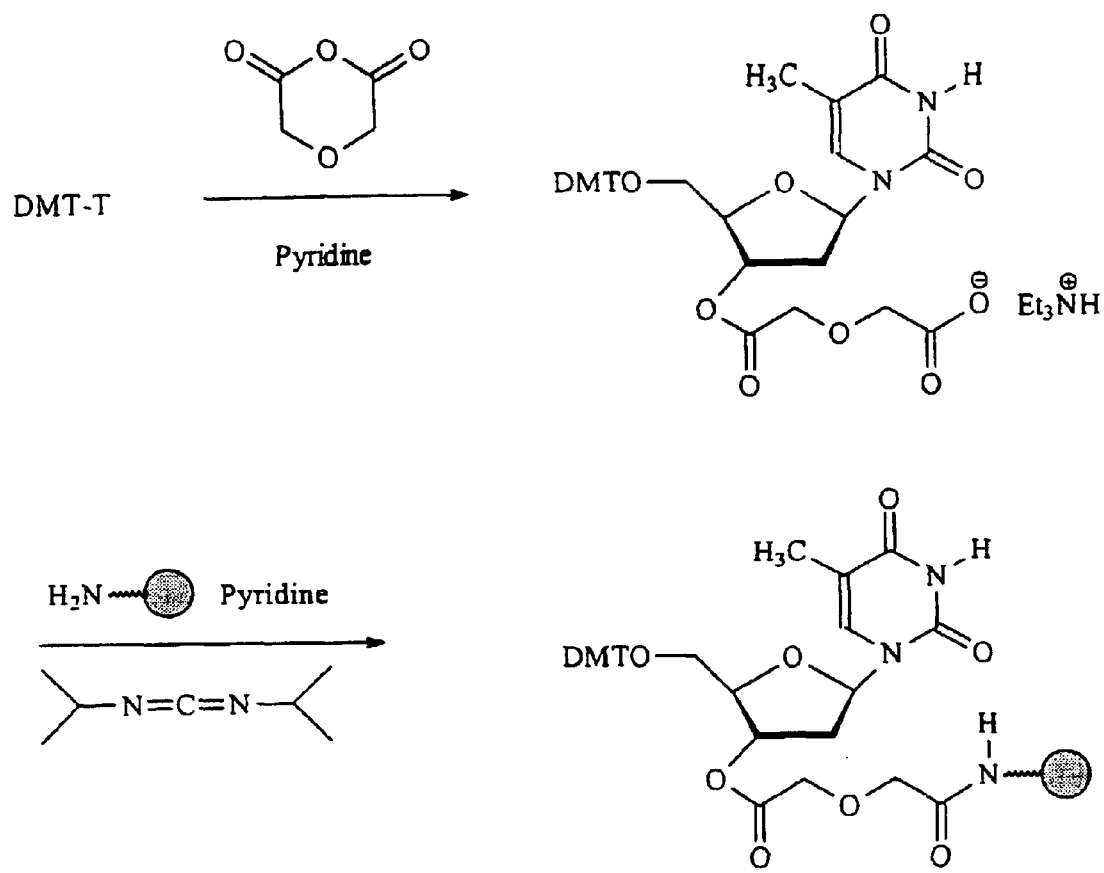
FIG. 1 is a synthetic scheme for support-bound nucleoside 1.

The present invention relates to methods for the preparation of oligonucleotides having at least one bioreversible protecting group. The bioreversible protecting groups contribute to certain enhanced chemical and biophysical properties of the oligonucleotides including resistance to exo- and endonuclease degradation.

Oligonucleotides represent a new class of compounds that specifically inhibit gene expression by Watson-Crick base pair formation with their targets which usually are known mRNA sequences. After binding to the mRNA, down regulation of gene product expression occurs. Crooke, S. T., *Nucleic Acid Therapeutics In Pharmaceutical Manufacturing International*, Sterling, London, 89 (1992). Use of the first synthesized oligonucleotides, i.e., phosphodiester linked oligonucleotides, was limited by the lack of nuclease resistance of these compounds. Nuclease resistance has mainly been resolved by the use of modified oligonucleotides. Milligan, et al., *J. Med. Chem.* 1991, 36, 1923; Varma, *Synlett* 1991, 621; Uhlmann, et al., *Chem. Rev.* 1990, 90, 534.

It has been reported that phosphodiester and phosphorothioate oligonucleotides, both of which have a polyanionic character, enter the cell by an active process (adsorptive endocytosis and/or fluid phase endocytosis) and this uptake varies with different cell types. It has been reported that the neutral methylphosphonodiester oligonucleotides enter cells by a different mechanism that is also energy dependent. Spiller, et al., *Anti-Cancer Drug Design* 1991, 7, 115. Certain increases in penetration of the oligonucleotides into cells has been achieved by derivatizing oligonucleotides with poly L-lysine, cholesterol or other like moieties or by encapsulation into liposomes.

In one aspect, the present invention is directed to a further approach to assist cellular uptake of oligonucleotides. In this approach a prodrug strategy is utilized wherein a prooligonucleotide is formed that is believed to temporarily mask the negative charges of phosphodiester, phosphorothioate and phosphorodithioate oligonucleotides by the introduction of a bioreversible group on at least some of the phosphate groups of these oligomers. The resulting neutral prooligonucleotides have been found to be enzymatically stable against degradative enzymes. While we do not wish to be bound by any particular theory, we believe that this will help oligonucleotides to escape from the endosomes should they become embedded therein and will present a completely different bioavailability pattern in relation with their route of administration. A perceived prerequisite of this approach is that bioreversible groups should be selected that have stability in culture medium and that have selective intracellularly hydrolysis after uptake, due to the existence of a greater enzymatic activity in cytosol than in biological fluids.

The present invention is directed to methods for the preparation of oligonucleotides having at least one bioreversible protecting group and enhanced chemical and biophysical properties for cellular membrane penetration as well as resistance to exo- and endonuclease degradation in vivo. In certain preferred embodiments of the invention, the bioreversible protecting groups are removed in the cell cytosol by endogenous carboxyesterases to yield biologically active oligonucleotide compounds that are capable of hybridizing to and/or having an affinity for specific nucleic acid or peptide sequences thus interacting with endogenous and/or pathogenic biomolecules.

In one aspect of the present invention, methods are provided for the preparation of compounds comprising a sequence of nucleotide units that includes a first segment having at least one phosphodiester internucleoside linkage and a second segment having at least one phosphotriester internucleoside linkage of formula:

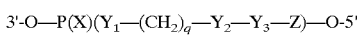

wherein each of X, $Y_1$, and $Y_2$ is, independently, O or S; q is 2 to about 4; $Y_3$ is C(=O) or S; and Z is aryl having 6 to about 14 carbon atoms or alkyl having from one to about six carbon atoms. The linkages of the first and second segments (and, hence, the segments themselves) preferably are placed at predetermined positions on an oligonucleotide. That is, they are not merely randomly generated, for example, after the coupling of nucleosides, but, rather, are positioned in the oligonucleotide in a stepwise fashion by coupling suitable (e.g., SATE-modified) nucleoside building blocks such that a predetermined number of nucleosides separate the respective linkages.

Particularly preferred compounds of the invention are those comprising moieties having formula:

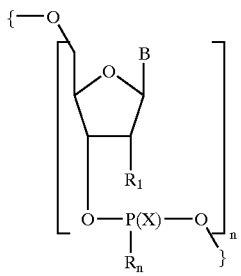

and formula:

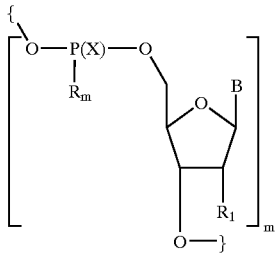

wherein:
each B is, independently, a naturally occurring or non-naturally occurring nucleobase;
each $R_1$ is, independently, H, OH, F, or a group of formula $R_7$—$(R_8)_n$;
each $R_7$ is, independently, $C_3$–$C_{20}$ alkyl, $C_4$–$C_{20}$ alkenyl, $C_2$–$C_{20}$ alkynyl, $C_1$–$C_{20}$ alkoxy, $C_2$–$C_{20}$ alkenyloxy, or $C_2$–$C_{20}$ alkynyloxy;
each $R_8$ is, independently, hydrogen, amino, protected amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, poly-ether, a group that enhances the pharmacodynamic properties of oligonucleotides, a group that enhances the pharmacokinetic properties of oligonucleotides, or a group of formula (—O—$X_3$)$_p$, where p is 2 to about 10 and $X_3$ is alkyl having from one to about 10 carbons;
each X is, independently, O or S;
n is 1 to about 100;
m is 1 to about 100; and
$R_n$ and $R_m$ are selected such that:
each $R_n$ is, independently, O$^-$ or O—(CH$_2$)$_p$—E and each $R_m$ is —Y$_1$—(CH$_2$)$_q$—Y$_2$—Y$_3$—Z; or
each $R_n$ is —Y$_1$—(CH$_2$)$_q$—Y$_2$—Y$_3$—Z and each $R_m$ is, independently, O$^-$ or O—(CH$_2$)$_p$—E;
wherein:
p is 1 to about 5;
E is a group that is electron-withdrawing with respect to hydrogen; and
each $Y_1$, $Y_2$, $Y_3$, q, and Z are, independently, as defined above.

In preferred embodiments, $Y_1$ and $Y_2$ are each O and $Y_3$ is C(=O), or $Y_1$ and $Y_2$ are each S and $Y_3$ is C(=O), or $Y_1$ is S and $Y_2$ is O and $Y_3$ is C(=O). In particularly preferred embodiments, $Y_1$ is O and $Y_2$ is S and $Y_3$ is C(=O).

The compounds of the invention can be prepared by contacting a support-bound starting compound of Formula II with a secondary amine compound in an organic solvent.

II

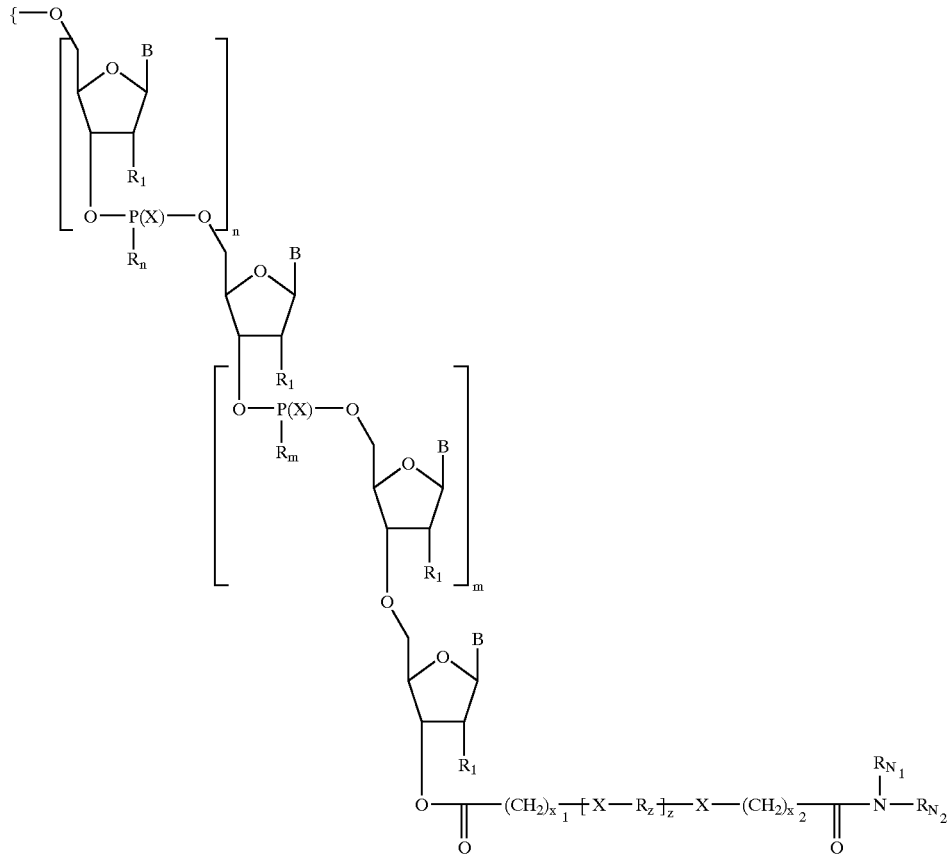

This contacting is performed for a time and under conditions effective to produce an intermediate compound of Formula II wherein the at least one $R_n$ or $R_m$ is $O^-$.

Secondary amine compounds according to the invention are compounds that possess at least one nitrogen atom covalently bound to three moieties yet to only a single hydrogen (i.e., H) atom. A wide variety of such compounds are known to those skilled in the art including, for example, those in which the groups to which the nitrogen atom are bound are alkyl having 1 to about 10 carbon atoms or aryl having 5 to about 20 carbon atoms, or the nitrogen atom constitutes a heteroatom in a heteroaromatic or heteroaromatic system having 4 to about 20 carbon atoms. Preferred secondary amine compounds include dimethylamine, diethylamine, di-n-propylamine, piperidine, piperazine, pyrrolidine, and morpholine. In preferred embodiments, an alkoxy linker moiety is employed in Formula II wherein X is O, z is 0, and $x_1$ and $x_2$ both are 1.

The organic solvents in which compounds of Formula II are contacted with the secondary amine compound preferably are aprotic. Representative solvents include ethers, nitrites, N,N-dialkylcarboxamindes, and dialkylsulfoxides, with dioxane, tetrahydrofuran (THF), acetonitrile, and dimethylformamide (DMF) being preferred.

In accordance with the invention, the support-bound compound that is produced following treatment with the secondary amine is contacted with a mild base in an organic solvent under conditions effective to produce a cleavage product having Formula III:

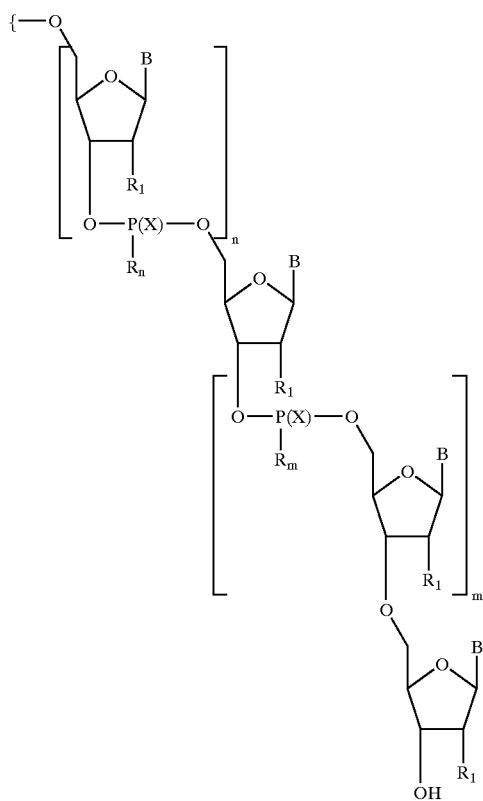

III

Mild bases according to the invention are those which possess negligible nucleophilic character, a pKa of about 9 to about 13, and are soluble in organic solvents such as alcohols. Representative mild bases include metal carbonates, metal hydroxides, tetraalkylammonium carbonates, and tetraalkylammonium hydroxides, with cesium and potassium carbonate (particularly at 0.01–0.05 M levels) being preferred.

The organic solvents in which compounds of Formula II are contacted with mild base preferably are polar. Representative solvents include alcohols, N,N-dialkylcarbonates, and dialkylsulfoxides, with methanol and trifluoroethanol being preferred.

It is believed to be important that the base-treatment step be performed using moisture-free solvents on systems that are substantially free of the secondary amine compound. While not wishing to be bound by any particular theory, the secondary amine compound catalyzes undesired cleavage of triester functionality present in the compounds of the invention. Conventional solvent washing does not appear to remove sufficiently quantities of the secondary amine compound from most supports, although the performance of a detritylation step (see, e.g., Protocols For Oligonucleotides And Analogs, Agrawal, S., ed., Humana Press, Totowa, N.J., 1993) before the base-treatment does.

Compounds of Formula II, in turn, can be prepared from linker-bearing nucleosides having Formula IV:

IV

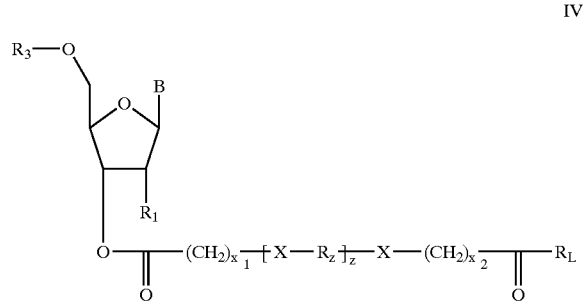

wherein $R_L$ is —OH and $R_3$ is hydrogen or a hydroxyl protecting group. Preferably, at least one of $x_1$ and $x_3$ is not 1 when z is 0 and $R_3$ is hydrogen or a hydroxyl protecting group. Compounds having Formula IV can be reacted with an amine-functionalized supports to form the amide linkage shown in Formula II.

In some preferred embodiments of the invention, a phosphoramidite compound is reacted with a growing nucleotide chain to produce a phosphite compound, as disclosed in application Ser. No. 09/066,638, filed on Apr. 24, 1998, the entire contents of which are incorporated herein by reference. Preferably, capping, and/or oxidation or sulfurization steps are performed, and the iterative cycle is repeated until the desired nucleobase sequence is attained. Representative solution phase techniques for preparing certain compounds according to the invention are described in U.S. Pat. No. 5,210,264, which is assigned to the assignee of the present invention and incorporated herein by reference. In preferred embodiments, the methods of the present invention are employed for use in iterative solid phase oligonucleotide synthetic regimes. Representative solid phase techniques are those typically employed for DNA and RNA synthesis utilizing standard phosphoramidite chemistry, (see, e.g., Protocols For Oligonucleotides And Analogs, Agrawal, S., ed., Humana Press, Totowa, N.J., 1993, hereby incorporated by reference in its entirety). A preferred synthetic solid phase synthesis utilizes phosphoramidites as activated phosphate compounds. In this technique, a phosphoramidite monomer is reacted with a free hydroxyl on the growing oligomer chain to produce an intermediate phosphite compound, which is subsequently oxidized to the $P^V$ state using standard methods. This technique is commonly used for the synthesis of several types of linkages including phosphodiester, phosphorothioate, and phosphorodithioate linkages.

In preferred embodiments, the methods of the invention are used for the preparation of oligonucleotides and their analogs. As used herein, the term "oligonucleotide" is intended to include both naturally occurring and non-naturally occurring (i.e., "synthetic") oligonucleotides. Naturally occurring oligonucleotides are those which occur in nature; for example ribose and deoxyribose phosphodiester oligonucleotides having adenine, guanine, cytosine, thymine and uracil nucleobases. As used herein, non-naturally occurring oligonucleotides are oligonucleotides that contain modified sugar, internucleoside linkage and/or nucleobase moieties. Such oligonucleotide analogs are typically structurally distinguishable from, yet functionally interchangeable with, naturally occurring or synthetic wild type oligonucleotides. Thus, non-naturally occurring oligonucleotides include all such structures which function effectively to mimic the structure and/or function of a desired RNA or DNA strand, for example, by hybridizing to a target.

Representative nucleobases include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in *Antisense Research and Application*, Ed. S. T. Crooke and B. Lebleu, CRC Press, 1993, in Englisch et al., *Angewandte Chemie*, International Edition, 1991, 30, 613–722 (see especially pages 622 and 623, and in the *Concise Encyclopedia of Polymer Science and Engineering*, J. I. Kroschwitz Ed., John Wiley & Sons, 1990, pages 858–859, Cook, *Anti-Cancer Drug Design* 1991, 6, 585–607, each of which are hereby incorporated by reference in their entirety). The term "nucleosidic base" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole.

Representative 2' sugar modifications (moiety $R_1$ in the formulas described herein) amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249, each of which are hereby incorporated by reference in their entirety. Further sugar modifications are disclosed in Cook, P. D., supra. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, hereby incorporated by reference in its entirety.

Sugars having O-substitutions on the ribosyl ring are also amenable to the present invention. Representative substitutions for ring O include S, $CH_2$, CHF, and $CF_2$, see, e.g., Secrist, et al., *Abstract 21, Program & Abstracts, Tenth International Roundtable, Nucleosides, Nucleotides and their Biological Applications*, Park City, Utah, Sep. 16–20, 1992, hereby incorporated by reference in its entirety.

As used herein, the term "alkyl" includes but is not limited to straight chain, branch chain, and alicyclic hydrocarbon groups. Alkyl groups of the present invention may be substituted. Representative alkyl substituents are disclosed in U.S. Pat. No. 5,212,295, at column 12, lines 41–50, hereby incorporated by reference in its entirety.

"Aryl" groups are aromatic cyclic compounds including but not limited to phenyl, naphthyl, anthracyl, phenanthryl, pyrenyl, and xylyl.

In general, the term "hetero" denotes an atom other than carbon, preferably but not exclusively N, O, or S. Accordingly, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds, and one or more heteroatoms. Preferred heterocycloalkenyl groups include, for example, pyrrolidino groups.

Figure 3:
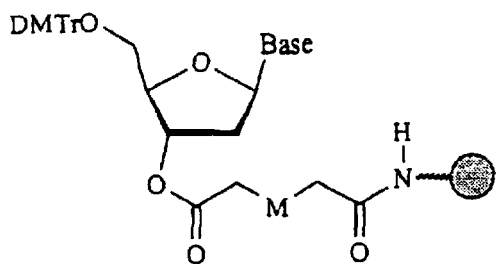
FIG. 3 is a scheme showing support-bound linkages 1 and 1 and further showing base protected phosphoramidites.
Figure 3:
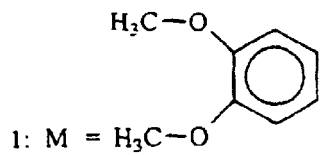
Figure 3:
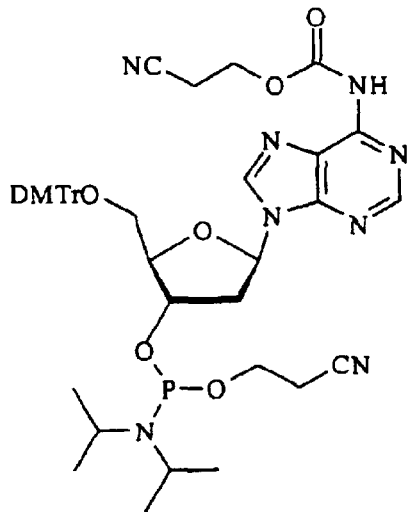
Figure 3:
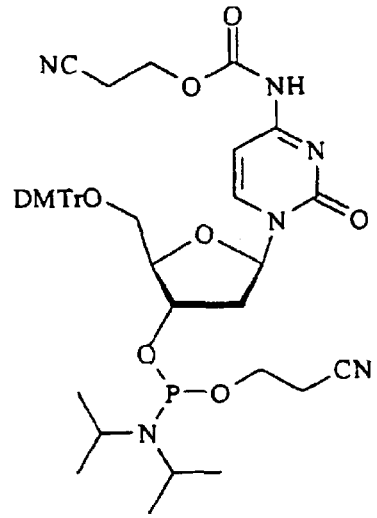

Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069. Linkers are known in the art as short molecules which serve to connect a solid support to functional groups (e.g., hydroxyl groups) of initial synthon molecules in solid phase synthetic techniques. A preferred base labile nucleoside derivatized solid support utilizes a nucleoside attached at the 3' position by a 1,2-phenylenedioxydiacetyl or diglycolyl linker (FIG. 3).

Solid supports according to the invention include those generally known in the art to be suitable for use in solid phase methodologies, including, for example, controlled pore glass (CPG), oxalyl-controlled pore glass (see, e.g., Alul, et al., *Nucleic Acids Research* 1991, 19, 1527), Tenta-Gel Support, an aminopolyethyleneglycol derivatized support (see, e.g., Wright, et al., *Tetrahedron Letters* 1993, 34, 3373, hereby incorporated by reference in its entirety) and Poros, a copolymer of polystyrene/divinylbenzene.

In some preferred embodiments of the invention $R_3$ can be a hydroxyl protecting group. A wide variety of hydroxyl protecting groups can be employed in the methods of the invention. Preferably, the protecting group is stable under basic conditions but can be removed under acidic conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage, et al., *Tetrahedron* 1992, 48, 2223–2311, and also in Greene and Wuts, *Protective Groups in Organic Synthesis*, Chapter 2, 2d ed, John Wiley & Sons, New York, 1991, each of which are hereby incorporated by reference in their entirety. Preferred protecting groups used for $R_2$, $R_3$ and $R_{3a}$ include dimethoxytrityl (DMT), monomethoxytrityl, 9-phenylxanthen-9-yl (Pixyl) and 9-(p-methoxyphenyl)xanthen-9-yl (Mox). The $R_3$ group can be removed from oligomeric compounds of the invention by techniques well known in the art to form the free hydroxyl.

For example, dimethoxytrityl protecting groups can be removed by protic acids such as formic acid, dichloroacetic acid, trichloroacetic acid, p-toluene sulphonic acid or with Lewis acids such as for example zinc bromide. See for example, Greene and Wuts, supra.

In some preferred embodiments of the invention amino groups are appended to alkyl or other groups, such as, for example, 2'-alkoxy groups (e.g., where $R_1$ is alkoxy). Such amino groups are also commonly present in naturally occurring and non-naturally occurring nucleobases. It is generally preferred that these amino groups be in protected form during the synthesis of oligomeric compounds of the invention. Representative amino protecting groups suitable for these purposes are discussed in Greene and Wuts, *Protective Groups in Organic Synthesis*, Chapter 7, 2d ed, John Wiley & Sons, New York, 1991. Generally, as used herein, the term "protected" when used in connection with a molecular moiety such as "nucleobase" indicates that the molecular moiety contains one or more functionalities protected by protecting groups.

In a preferred embodiment the nucleobases are protected using protecting groups selected form one of two different sets of protecting groups. The first set includes phenoxyacetyl (PAC) (Wu et al., *Tetrahedron Letters*, 1988, 29, 4249–4252), 4-(isopropyl)phenoxyacetyl (available from Sigma Chemical Company, St. Louis, Mo.), or 4-(t-butyl) phenoxyacetyl (tBPA) (Sinha et al., *Biochimie*, 1993, 75, 13–23), for all three bases. The second set includes (2-cyanoethoxy)carbonyl (CEOC) protection for dA and dC phosphoramidites while dG amidites is used unprotected.

The deprotection consists of treatment with a solution of a secondary amine (preferably piperidine, diethylamine, pyrrolidine, N,N'-dimethyl-1,2-diaminoethane, piperazine, or morpholine) in an anhydrous organic solvent (preferably dioxane, THF, or acetonitrile). This treatment selectively removes both acyl and 2-cyanoethyl protecting groups from the base and phosphate or phosphorothioate internucleotide linkages. Pretreatment with 2M diisopropylamine in an organic solvent is required for CEOC-protected oligonucleotides. Following this treatment oligonucleotides are released from the solid support by treatment with a solution of an inorganic base in an organic solvent. A preferred solution includes 0.01 to 0.05 M $K_2CO_3$ in MeOH. Isolated yield of patchmer oligonucleotides is 5 to 70% depending on the length and the number of S-pivaloylmercaptoethyl (SPME) groups introduced.

Oligonucleotides or oligonucleotide analogs according to the present invention hybridizable to a specific target preferably comprise from about 5 to about 50 monomer subunits. It is more preferred that such compounds comprise from about 10 to about 30 monomer subunits, with 15 to 25 monomer subunits being particularly preferred. When used as "building blocks" in assembling larger oligomeric compounds (i.e., as synthons of Formula II), smaller oligomeric compounds are preferred. Libraries of dimeric, trimeric, or higher order compounds of general Formula II can be prepared for use as synthons in the methods of the invention. The use of small sequences synthesized via solution phase chemistries in automated synthesis of larger oligonucleotides enhances the coupling efficiency and the purity of the final oligonucloetides. See for example: Miura, et al., *Chem. Pharm. Bull.* 1987, 35, 833–836; Kumar, et al., *J. Org. Chem.* 1984, 49, 4905–4912; Bannwarth, *Helvetica Chimica Acta* 1985, 68, 1907–1913; Wolter, et al., *Nucleosides and Nucleotides* 1986, 5, 65–77, each of which are hereby incorporated by reference in their entirety.

The oligonucleotides of the invention having bioreversible protecting groups also can be referred to as pro-oligonucleotides. Such pro-oligonucleotides are capable of improved cellular lipid bilayers penetrating potential as well as resistance to exo- and endonuclease degradation in vivo. In cells, the bioreversible protecting groups are removed in the cell cytosol by endogenous carboxyesterases to yield biologically active oligonucleotide compounds that are capable of hybridizing to and/or having an affinity for specific nucleic acid.

The compounds produced by the methods of the invention mitigate one potential problem with the therapeutic use of oligonucleotides of natural composition, i.e., phosphodiester oligonucleotides; specifically 1) their very short biological half-lives due to degradation by nucleases which tend to be ubiquitous, and 2) their inherent negative charge and hydrophilic nature which makes it very difficult biophysically for oligonucleotides to pass through lipid cellular membranes.

The methods of the invention can be used to prepare antisense pro-oligonucleotides to synthetic DNA or RNA or mixed molecules of complementary sequences to a target sequence belonging to a gene or to an RNA messenger whose expression they are specifically designed to block or down-regulate. The methods of the invention can be used to prepare antisense oligonucleotides that can be directed against a target messenger RNA sequence or, alternatively against a target DNA sequence, and hybridize to the nucleic acid to which they are complementary. Accordingly, the compounds produced by the methods of the invention effectively block or down-regulate gene expression.

The pro-oligonucleotides produced according to the methods of the invention can also be directed against certain bicatenary DNA regions (homopurine/homopyrimidine sequences or sequences rich in purines/pyrimidines) and thus form triple helices. The formation of a triple helix, at a particular sequence, can block the interaction of protein factors which regulate or otherwise control gene expression and/or may facilitate irreversible damage to be introduced to a specific nucleic acid site if the resulting oligonucleotide is made to possess a reactive functional group.

As used herein, a target nucleic acid is any nucleic acid that can hybridize with a complementary nucleic acid-like compound. Further in the context of this invention, "hybridization" shall mean hydrogen bonding, which may be Watson-Crick, Hoogsteen or reversed Hoogsteen hydrogen bonding, between complementary nucleobases. "Complementary" as used herein, refers to the capacity for precise pairing between two nucleobases. For example, adenine and thymine are complementary nucleobases which pair through the formation of hydrogen bonds. "Complementary" and "specifically hybridizable," as used herein, refer to precise pairing or sequence complementarity between a first and a second nucleic acid-like oligomers containing nucleoside subunits. For example, if a nucleobase at a certain position of the first nucleic acid is capable of hydrogen bonding with a nucleobase at the same position of the second nucleic acid, then the first nucleic acid and the second nucleic acid are considered to be complementary to each other at that position. The first and second nucleic acids are complementary to each other when a sufficient number of corresponding positions in each molecule are occupied by nucleobases which can hydrogen bond with each other. Thus, "specifically hybridizable" and "complementary" are terms which are used to indicate a sufficient degree of complementarity such that stable and specific binding occurs between a compound of the invention and a target RNA molecule. It is understood that an oligomeric compound of the invention need not be 100% complementary to its target RNA sequence to be specifically hybridizable. An oligomeric compound is specifically hybridizable when binding of the oligomeric compound to the target RNA molecule interferes with the normal function of the target RNA to cause a loss of utility, and there is a sufficient degree of complementarity to avoid non-specific binding of the oligomeric compound to non-target sequences under conditions in which specific binding is desired, i.e. under physiological conditions in the case of in vivo assays or therapeutic treatment, or in the case of in vitro assays, under conditions in which the assays are performed.

As used herein, the term "contacting" refers to the placement together of moieties, directly or indirectly, such that they become physically associated with each other. Thus, "contacting" includes, inter alia, placement together in a container.

The oligonucleotides of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLES

General Procedures

All reagents and solvents were purchased from Aldrich Chemical Co. Flash chromatography was performed on silica gel (Baker 40 $\mu$m). Thin layer chromatography was performed on Kieselgel 60 F-254 glass plates from E. Merck and compounds were visualized with UV light and sulfuric acid-methanol spray followed by charring. Solvent systems used for thin-layer chromatography and flash chromatography were: (A) ethyl acetate-hexanes 1:1; (B) ethyl acetate-hexanes-TEA 2:3:0.5. $^1$H and $^{31}$P spectra were recorded using a Gemini 200 Varian spectrometer. All reactions were performed under an argon atmosphere and solutions rotary evaporated at 35–45° C. in vacuo using a vacuum pump-vacuum controller combination.

Example 1

3'-O-Diglycolyl-5'-(4,4'-dimethoxytrityl)thymidine derivatized CPG (1)

As shown in FIG. 1, 5'-(4,4'-dimethoxytrityl)-thymidine (1.09 g, 2.0 mmol), diglycolic anhydride (689 mg, 6.0 mmol), and pyridine (10 mL) were stirred for 7 hours at room temperature. The mixture was quenched with water (2 mL) for 10 min and evaporated to oil. The residue was dissolved in ethyl acetate (50 mL), washed with triethylammonium acetate (2 M aqueous, 5×10 mL), then with water (5×10 mL), dried over $Na_2SO_4$, and evaporated. The residue was dissolved in pyridine (10 mL), long chain alkyl amine controlled pore glass (LCA CPG, CPG, Inc., Lincoln Park, N.J., 115.2 $\mu$mol/g, mean pore diameter 523 Å, particle size 120/200, 3.0 g) was added, and the mixture was degassed in vacuo. N,N'-Diisopropylcarbodiimide (800 mg, 6.3 mmol) was added, and the mixture was shaken overnight at room temperature. The solid support was filtered out, treated with a mixture of acetic anhydride, N-methylimidazole, 2,6-lutidine and THF (1:1:2:16 v/v) for 30 min, filtered, washed on filter with acetonitrile (5×10 mL), and dried on an oil pump. Efficiency of the derivatization was determined by dimethoxytrityl assay to show a loading of 69 $\mu$mol/g.

Example 2

Oligonucleotide Synthesis

Chimerical oligothymidylates were assembled on an ABI 380B DNA Synthesizer using 5'-O-(4,4'-dimethoxytrityl)-thymidine 3'-O-(carboxymethyloxy)acetate derivatized CPG 1 (diglycolyl-T CPG) 1, phosphoramidite chemistry, and either commercial oxidizer or 3H-1,2-benzodithiol-3-one 1,1-dioxide (0.05 M in MeCN) as the sulfur-transfer reagent. Either 5'-O-(4,41-dimethoxytrityl)thymidyl 2-(pivaloylthio)ethyl N,N-diisopropylaminophosphite or 3'-O-[5-methyl-2'-O-(2-methoxy-ethyl)-5'-O-(4,4'-dimethoxytrityl)uridyl] 2-(pivaloyl-thio)ethyl N,N-diisopropylaminophosphite were employed for chain assembly to create 2-(pivaloylthio)ethyl triester internucleosidic moieties. Otherwise, commercial thymidine cyanoethyl phosphoramidite was used.

Figure 2:
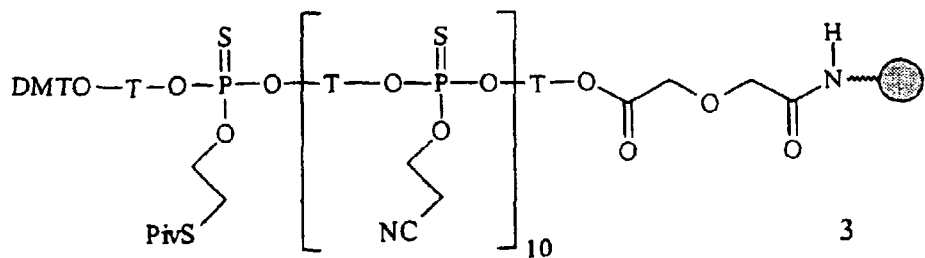
FIG. 2 is a synthetic scheme for oligonucleotide 5 having segments of phosphodiester-linked nucleosides and phosphotriester-linked nucleosides.
Figure 2:
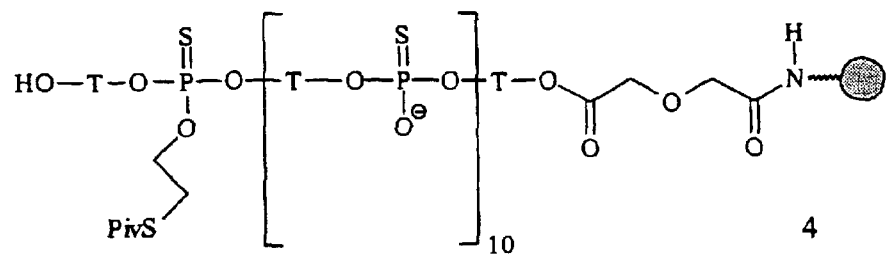
Figure 2:
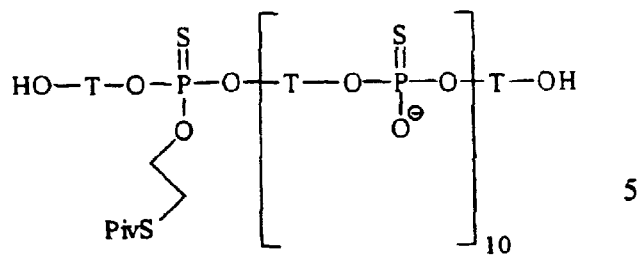

Deprotection procedure is exemplified in FIG. 2 for chimera 5. After completeness of oligonucleotide synthesis, a solid support-bound 3 was decyanoethylated with either 2M diethylamine or 1M piperidine in MeCN (3 mL) for 4 h. The column was washed with dioxane (10 mL) and replaced on the instrument, and the standard detritylation subroutine was carried out to give 4.

After extensive washing with MeCN and drying the oligonucleotide 5 was released from the solid support 4 by treatment with 0.01 M $K_2CO_3$ in MeOH (2×5 mL and 2×20 mL for 1 and 15 $\mu$mol syntheses, respectively). Each portion was passed forth and back through the column for 45 min, neutralized by passing through short column with Dowex 50W×8 (PyH$^+$; ca. 1 mL). The combined eluates were evaporated to dryness, co-evaporated with MeCN (10 mL), and dissolved in water. The obtained mixture consisted of 5 along with products of methanolysis of 2-(pivaloylthio)ethyl groups (ca. 1 to 1.5% of methanolysis per each group). Target oligonucleotide 5 was isolated by RP HPLC on a Delta Pak 15 mm C18 300 Å column (3.9×300 mm and 7.8×300 mm for 1 and 15 $\mu$mol syntheses, respectively), using 0.1 M $NH_4OAc$ as buffer A, 80% aq MeCN as buffer B, and a linear gradient from 0 to 100% B in 50 min at a flow rate 1.5 and 5 mL min$^{-1}$, respectively. Collected fractions were evaporated, re-dissolved in water and desalted by injecting on to the same column, then washing with water (10 min) and eluting an oligonucleotide 5 as an ammonium salt with 50% aq MeCN (20 min). Homogeneity of chimerical oligonucleotides was characterized by RP HPLC and capillary electrophoresis, and their structure was confirmed by mass spectrometry and $^{31}$P NMR (see, tables I and II).

TABLE I

| SEQ ID NO: | Oligo # | Sequence (5'–3') | linkage chemistry |
|---|---|---|---|
| 1 | 1 | T*TT TTT TTT TT | P=S |
| 2 | 2 | TTT TTT TTT TTT | P=O |
| 2 | 3 | T*TT TTT TTT TTT | P=O |
| 2 | 4 | TTT TTT TTT TTT | P=S |
| 2 | 5 | TTT TTT TTT TT*T | P=S |
| 2 | 6 | TTT TTT TTT T*TT | P=S |
| 2 | 7 | TTT TTT TTT* TTT | P=S |
| 2 | 8 | TTT TTT TTT* T*TT | P=S |
| 2 | 9 | TTT TTT TTT* TT*T | P=S |
| 2 | 10 | TTT TTT TTT* T*T*T | P=S |
| 2 | 11 | TTT TTT TTT* T*T*T | P=S |
| 2 | 12 | TTT TT*T* T*TT TTT | P=S |
| 3 | 13 | T*T*T* TTT TTT TTT TTT T*T*T* T | P=S |
| 3 | 14 | T#T#T# T#TT TTT TTT TTT# T#T#T# T | P=S |

*indicates a 2-(pivaloylthio)ethyl phosphotriester internucleotide linkage.
indicates a 2-(pivaloylthio)ethyl phosphotriester internucleotide linkage and a 2'-O-(2-methoxyethyl)thymidine residue.

TABLE II

| Oligo # | Isolated Yield % | Retention Time(min) | Molec. Mass found/calcd. | $^{31}$P NMR δ ppm |
|---|---|---|---|---|
| 1 | 61.3 | 22.0; 22.4; 22.6 | 3908.0/3909.33 | — |
| 2 | — | 15.0 | —/— | — |
| 3 | 65.5 | 20.33 | 3731.6/3732.56 | — |
| 4 | — | 17.0 | —/— | — |
| 5 | 51.2 | 22.4 | 3909.1/3909.33 | 67.33 (1 P); 55.95 (10 P) |
| 6 | 59.4 | 22.3 | 3909.3/3909.33 | — |
| 7 | 60.2 | 20.5 | 3909.3/3909.33 | — |
| 8 | 60.8 | 27.14;27.45 | 4053.4/4053.57 | — |
| 9 | 54.9 | 26.7;27.3 | 4053.4/4053.57 | 67.17 (2 P); 55.92 (9 P) |
| 10 | 55.1 | 29.2; 29.6 | 4053.5/4053.57 | 67.48 (2 P); 55.94 (9 P) |
| 11 | 57.2 | 33.4 | 4197.6/4197.81 | — |
| 12 | 62.6 | 29.65 | 4197.6/4198.31 | — |
| 13 | 46.4 | 36.9 | 7194.1/7192.61 | 67.18 (6 P); 56.15 (13 P) |
| 14 | 39.5 | 43.5 | 8072.9/8073.73 | — |

The efficiency of the deprotection method was verified by preparing chimeric oligonucleotide phosphorothioates (oligo #'s 1 and 5–14 and phosphodiester oligonucleotide (oligo # 3) in 1 to 15 μmol scale.

Example 3

Preparation of 5'-O-(DMT)-N$^4$-phenoxyacetyl-2'-deoxycytidine Derivatized 1,2-phenylenedioxydiacetyl CPG A mixture of 5'-O-(DMT)-N$^4$-phenoxyacetyl-2'-deoxycytidine (2.665 g, 4.0 mmol), 1,2-phenylenedioxydiacetic acid (1.81 g, 8.0 mmol), N,N'-dicyclohexylcarbodiimide (1.03 g, 5.0 mmol), pyridine (2.5 mL), and THF (20 mL) was stirred for 7 hours at room temperature. The mixture was quenched with water (2 mL) for 10 minutes, filtered and concentrated to an oil. The oil was dissolved in ethyl acetate (75 mL), washed with triethylammonium acetate (2 M aqueous, 5×20 mL), then with water (5×20 mL), dried over Na$_2$SO$_4$, and evaporated. The residue was dissolved in pyridine (20 mL), long chain alkyl amine Controlled Pore Glass (CPG, 6.0 g) was added, and the mixture was degassed in vacuo. N,N'-Diisopropylcarbodiimide (1.20 g) was added, and the mixture was shaken overnight at room temperature. The solid support was filtered out, treated with a mixture of acetic anhydride, N-methylimidazole, 2,6-lutidine and THF (1:1:2:16 v/v) for 30 minutes, filtered, washed on the filter with acetonitrile (5×10 mL), and dried under high vacuum. The efficiency of derivatization was determined by dimethoxytrityl assay to show a loading of 71 mmol/g.

Example 4

Synthesis of Oligonucleotides

Oligodeoxynucleotides were assembled on an ABI 380B DNA Synthesizer using nucleoside derivatized CPG 1 and 2 (FIG. 3) 1) (Pon, R. T. and Yu, S., *Nucleic Acids Res.*, 1997, 25, 3629–3635) phosphoramidite chemistry, and either commercial oxidizer or 3H-1,2-benzodithiol-3-one-1,1-dioxide (0.05 M in MeCN) as the sulfur-transfer reagent. Deoxyadenosine, deoxycytidine, and deoxyguanosine CE phosphoramidites were uniformly protected at the exocyclic amino groups with either phenoxyacetyl (PAC) or 4-(t-butyl)phenoxyacetyl (tBPA) groups. Deoxyadenosine and deoxycytidine SPME phosphoramidites were protected at the exocyclic amino groups with phenoxyacetyl (PAC) groups. Alternatively, deoxyadenosine and deoxycytidine CE and SPME phosphoramidites were protected at the exocyclic amino groups with 2-cyanoethoxycarbonyl group (FIG. 3).

Example 5

Deprotection of SPME-Modified (CEOC)N-PAC and N-tBPA Protected Oligonucleotides

Figure 4:
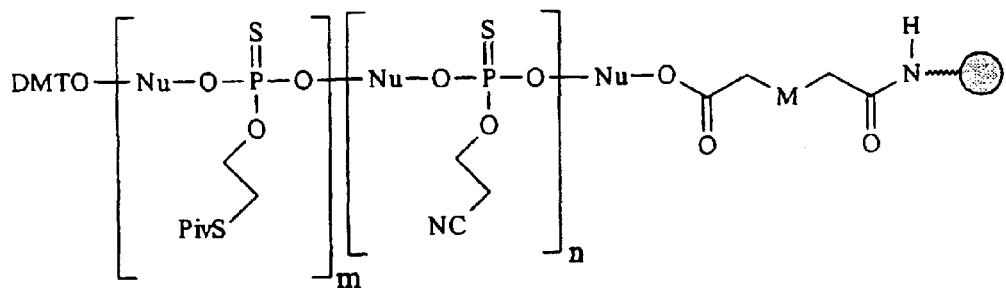
FIG. 4 is a synthetic scheme for oligonucleotide # 15 having segments of phosphodiester-linked mixed base nucleosides and phosphotriester-linked nucleosides.
Figure 4:
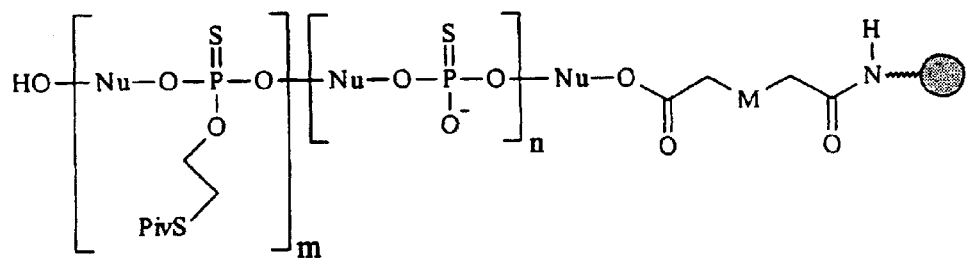
Figure 4:
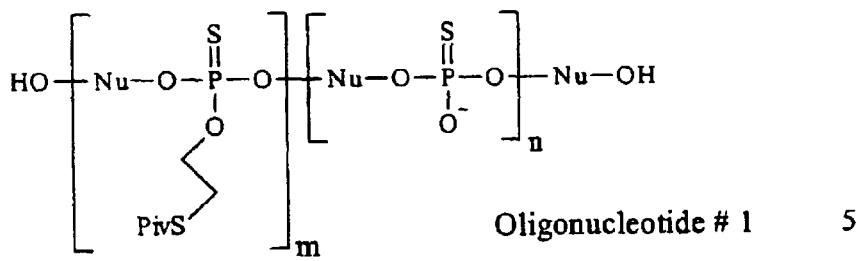
Figure 4:
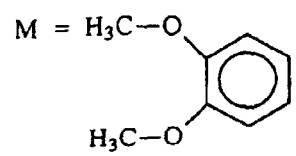

The two step deprotection of SPME-modified oligonucleotides (Formula 6, FIG. 4) with secondary amines in an organic solvent followed by treatment with methanolic K$_2$CO$_3$ is illustrated in FIG. 4. Following the synthesis of a desired oligonucleotide of the invention, the solid support bound oligonucleotide is treated with either 2M diethylamine in or 1M piperidine in MeCN, dioxane, THF, or DMF (3 mL) for 8 to 12 h. The column is washed with dioxane (10 mL), reinstalled on the synthesizer, and the solid support is detritylated. The oligonucleotide is released from the solid support by treatment with 0.01 M K$_2$CO$_3$ in MeOH (4×5 mL and 4×20 mL for 1 and 15 mmol syntheses, respectively). Each portion is passed back and forth through the column for 20 minutes, and the oligonucleotide containing solutions are combined. The solutions are neutralized by either of two methods:

a) A solution of glacial acetic acid is gradually added to the combined solutions until slightly acidic reaction of the solution. The precipitate of the oligonucleotide is sedimented by centrifugation and redissolved in 50% aqueous DMSO. The target oligonucleotide is isolated by RP HPLC on a Delta Pak 15 mm C18 300 Å column (3.9×300 mm and 7.8×300 mm for 1 and 15 μmol syntheses, respectively), using 0.1 M NH$_4$OAc as buffer A, 80% aq MeCN as buffer B, and a linear gradient from 0 to 60% B in 40 min at a flow rate 1.5 and 5 mL/minute, respectively. The solvent is evaporated, the product is re-dissolved in water. The oligonucleotide is desalted by injecting the resulting aqueous solution on to the same column and washing with water (10 min) followed by elution of the oligonucleotide as the ammonium salt using 50% aq MeCN (20 min) as the eluent. Homogeneity of the purified desalted oligonucleotide is determined by characterization using RP HPLC and capillary electrophoresis.

b) The combined solutions are passed through a short column with Dowex 50Wx8 (PyH$^+$; ca. 10 mL). The combined eluates are evaporated to dryness, co-evaporated with MeCN (10 mL), and dissolved in 50% aqueous DMSO.

Oligonucleotide 15 was synthesized as illustrated in Example 4 above and deprotected using the above procedures. The oligonucleotide was neutralized and purified using either method "a" or "b".

The deprotection procedures above were used for deprotection of oligonucleotide phosphorothioates 15, 16 and 17 on 1 to 15 µmol scale.

TABLE III

| SEQ ID NO: | Oligo # | Sequence (5'–3') | Linkage chemistry | ESMS (found/calcd) |
|---|---|---|---|---|
| 4 | 15 | CCC CCA AT*T TTT TTT TTT | P=S | 5771.31/ 5773.81 |
| 5 | 16 | C*C*C* CCA CCA CTT CCC CT*C* T*C | P=S | 6999.55/ 7000.35 |
| 5 | 17 | C*C*C CCA CCA CTT CCC CTC* T*C | P=S | 6711.34/ 6711.87 |

*indicates a 2-(pivaloylthio)ethyl phosphotriester internucleotide linkage.

Example 5

Deprotection of SPME-Modified N-CEOC-Protected Oligonucleotides

After completeness of oligonucleotide synthesis a solid support-bound material was treated with 2M diisopropylamine in MeCN, dioxane, THF, or DMF (3 mL) for 12 h. The column was washed with dioxane (10 mL) and treated with 1M piperidine in MeCN (3 mL) for another 8 to 12 h. The column was reinstalled on the synthesizer, and the solid support was detritylated. The oligonucleotide was released from the solid support by treatment with 0.01 M $K_2CO_3$ in MeOH (4×5 mL and 4×20 mL for 1 and 15 mmol syntheses, respectively). Each portion was passed forth and back through the column for 20 min, and the oligonucleotide containing solutions were combined. The solutions were neutralized by either of two methods:

a) glacial acetic acid was gradually added until slightly acidic reaction of the solution. The precipitate of the oligonucleotide was sedimented by centrifugation and redissolved in 50% aqueous DMSO. Target oligonucleotide was isolated by RP HPLC on a Delta Pak 15 mm C18 300 Å column (3.9×300 mm and 7.8×300 mm for 1 and 15 µmol syntheses, respectively), using 0.1 M NH$_4$OAc as buffer A, 80% aq MeCN as buffer B, and a linear gradient from 0 to 60% B in 40 min at a flow rate 1.5 and 5 mL min$^{-1}$, respectively. The solvent was evaporated, the product was re-dissolved in water and desalted by injecting on to the same column, then washing with water (10 min) and eluting an oligonucleotide as an ammonium salt with 50% aq MeCN (20 min). Homogeneity of the product was characterized by RP HPLC and capillary electrophoresis.

b) the solution was passed through short column with Dowex 50Wx8 (PyH$^+$; ca. 10 mL). The combined eluates were evaporated to dryness, co-evaporated with MeCN (10 mL), and dissolved in 50% aqueous DMSO. The purification of the oligonucleotide was carried out as described above.

The deprotection procedures above were used for the preparation of oligonucleotide phosphorothioates 15, 16, and 17 on 1 µmol scale (Table III).

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound having the formula:

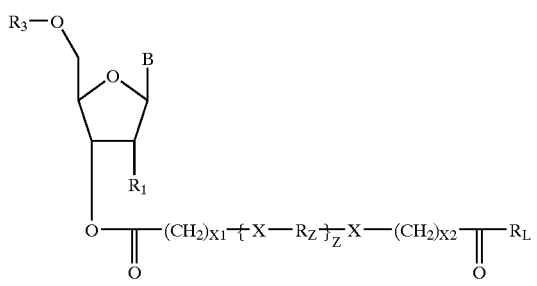

wherein:
each B is, independently, a naturally occurring or non-naturally occurring nucleobase;
each $R_1$ is, independently, H, OH, F, or a group of formula $R_7$—$(R_8)_n$;
each $R_7$ is, independently, a diradical of $C_3$–$C_{20}$ alkyl $C_4$–$C_{20}$ alky, $C_2$–$C_{20}$ alkynyl, $C_1$–$C_{20}$ alkoxy, $C_2$–$C_{20}$ alkenyloxy, or $C_2$–$C_{20}$ alkynyloxy;
each $R_8$ is, independently, hydrogen, amino, protected amino, halogen, hydroxyl, thiol, keto, carboxyl, nitro, nitroso, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, N-phthalimido, azido, hydrazino, hydroxylamino, isocyanato, aryl, a radical derived from imidazole, polyamide, polyalkylene glycol, polyether, or a group of formula (—O—$X_3)_{p1}$, where $p_1$ is 2 to about 10 and $X_3$ is alkylene having from one to about 10 carbons or alkyl having form one to about 10 carbons;
each X is, independently, O or S;
$R_z$ is a divalent aromatic radical having about 5 to about 8 carbon atoms or has formula $(CH_2)_{x3}$;

z is 0 or 1;
$x_1$, $x_2$, and $x_3$ are, independently, 1 to about 5;
$R_L$ is —OH or —N($R_{N1}$)($R_{N2}$);
$R_{N1}$ is H or alkyl having 1 to about 10 carbon atoms;
$R_{N2}$ is a solid support; and
$R_3$ is hydrogen, a hydroxyl protecting group, or group of the formula:

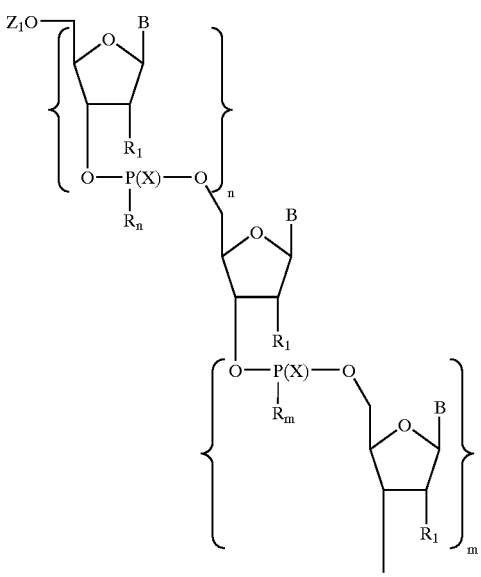

wherein:
each X is, independently, O or S;
$Z_1$ is H or a hydroxyl protecting group;
n is 1 to about 100;

m is 1 to about 100; and $R_n$ and $R_m$ are selected such that:
  each $R_n$ is, independently, $O^-$ or $O-(CH_2)_{p2}-E$ and each $R_m$ is $-Y_1-(CH_2)_q-Y_2-Y_3-Z$; or
  each $R_n$ is $-Y_1-(CH_2)_q-Y_2-Y_3-Z$ and each $R_m$ is, independently, $O^-$ or $O-(CH_2)_{p2}-E$;

wherein:
  p2 is 1 to about 5;
  E is $-CN$;
  each $Y_1$ is O;
  each q is, independently, 2 to about 4;
  each $Y_2$ is, independently O or S;
  each $Y_3$ is, independently, C(=O) or S; and
  each Z is, independently, aryl having 6 to about 14 carbon atoms or alkyl having from one to about six carbon atoms;

provided that at least one of $x_1$ and $x_2$ is not 1 when $R_3$ is hydrogen or a hydroxyl protecting group and z is 0, and provided that at least one nucleoside is a β-nucleoside and bound at its 3' position to a linking group of formula $-O-P(X)(R_n)-O-$ or $-O-P(X)(R_m)-O-$ where $R_n$ or $R_m$ is $O^-$ or $-O-(CH_2)_{p2}-E$.

2. The compound of claim 1 wherein each X is O.

3. The compound of claim 1 wherein $x_1$ and $x_3$ are 1 or 2, and z is 0.

4. The compound of claim 1 wherein $R_L$ is $-N(R_{N1})(R_{N2})$.

5. The compound of claim 1 wherein:
  $Y_2$ is O and $Y_3$ is C(=O); or
  $Y_2$ is S and $Y_3$ is C(=O).

6. The compound of claim 5 wherein q is 2 and Z is alkyl having 1 to about 6 carbon atoms.

7. The compound of claim 5 wherein Z is methyl, phenyl, or t-butyl.

8. The compound of claim 1 wherein $p_1$ is 2.

9. The compound of claim 1 wherein n and m are each about 2 to about 25.

* * * * *

UNITED STATES PATENT AND TRADEMARK OFFICE
CERTIFICATE OF CORRECTION

PATENT NO. : 6,919,437 B1
DATED : July 19, 2005
INVENTOR(S) : Muthiah Manoharan et al.

Page 1 of 1

It is certified that error appears in the above-identified patent and that said Letters Patent is hereby corrected as shown below:

Column 23,
Line 52, delete "alky" and insert -- alkenyl --.

Signed and Sealed this

Sixteenth Day of May, 2006

JON W. DUDAS
*Director of the United States Patent and Trademark Office*